US008845510B2

(12) United States Patent
Zilbershlag

(10) Patent No.: US 8,845,510 B2
(45) Date of Patent: Sep. 30, 2014

(54) FLEXIBLE GALVANIC PRIMARY AND NON GALVANIC SECONDARY COILS FOR WIRELESS COPLANAR ENERGY TRANSFER (CET)

(71) Applicant: Leviticus Cardio Ltd., Givat Shmuel (IL)

(72) Inventor: Michael Zilbershlag, Givat Shmuel (IL)

(73) Assignee: Leviticus Cardio Ltd., Givat Shmuel (IL)

( * ) Notice: Subject to any disclaimer, the term of this patent is extended or adjusted under 35 U.S.C. 154(b) by 0 days.

(21) Appl. No.: 14/097,431

(22) Filed: Dec. 5, 2013

(65) Prior Publication Data

US 2014/0163307 A1 Jun. 12, 2014

Related U.S. Application Data

(60) Provisional application No. 61/735,790, filed on Dec. 11, 2012.

(51) Int. Cl.
*A61M 1/12* (2006.01)
*A61M 1/10* (2006.01)

(52) U.S. Cl.
CPC ........... *A61M 1/1055* (2014.02); *A61M 1/1053* (2013.01); *A61M 1/127* (2013.01)
USPC ................... 600/16; 607/33; 607/44; 307/149

(58) Field of Classification Search
CPC .......................... A61M 1/1055; A61M 1/1053
USPC ........................... 600/16; 607/33, 44; 307/149
See application file for complete search history.

(56) References Cited

U.S. PATENT DOCUMENTS

| | | | |
|---|---|---|---|
| 4,906,229 | A | 3/1990 | Wampler |
| 4,957,504 | A | 9/1990 | Chardack |
| 5,095,903 | A | 3/1992 | DeBellis |
| 5,749,855 | A | 5/1998 | Reitan |
| 6,070,103 | A | 5/2000 | Ogden |
| 6,421,889 | B1 | 7/2002 | Chien |
| 6,527,699 | B1 | 3/2003 | Goldowsky |
| 6,761,681 | B2 | 7/2004 | Schmid et al. |
| 6,772,011 | B2 | 8/2004 | Dolgin |
| 7,613,497 | B2 | 11/2009 | Govari et al. |
| 7,650,192 | B2 | 1/2010 | Wahlstrand |
| 7,741,734 | B2 | 6/2010 | Joannopoulos et al. |
| 7,825,543 | B2 | 11/2010 | Karalis et al. |
| 7,825,776 | B2 | 11/2010 | Smith et al. |
| 7,956,725 | B2 | 6/2011 | Smith |
| 8,075,472 | B2 | 12/2011 | Zilbershlag et al. |

(Continued)

*Primary Examiner* — Christopher D Koharski
*Assistant Examiner* — Michael Carey
(74) *Attorney, Agent, or Firm* — Brown Rudnick LLP

(57) ABSTRACT

Systems and methods of the invention generally involve a convertible power transfer system for supplying wireless energy to an implant. According to certain aspect, a system of the invention includes a convertible inductive coil and a receiver inductive coil. The convertible inductive coil may be disposed externally on a body of a patient and to inductively transmit electromagnetic power. The convertible inductive coil transitions between direct electromagnetic power transfer and passive electromagnetic power transfer. The receiver inductive coil can be implanted within the body and provides received electromagnetic power to the implant. The convertible inductive coil, during passive electromagnetic power transfer, couples to the receiver inductive coil such that the convertible inductive coil and receiver inductive coil operate together as single receiver inductive coil that receives inductively transferred electromagnetic power from a distant transmitter inductive coil.

23 Claims, 11 Drawing Sheets

(56) References Cited

U.S. PATENT DOCUMENTS

| | | |
|---|---|---|
| 8,244,367 B2 | 8/2012 | Wahlstrand et al. |
| 8,278,784 B2 * | 10/2012 | Cook et al. .................. 307/149 |
| 8,285,388 B2 * | 10/2012 | Wahlstrand .................. 607/61 |
| 2004/0014315 A1 | 1/2004 | Lai et al. |
| 2004/0054251 A1 | 3/2004 | Liotta |
| 2004/0115038 A1 | 6/2004 | Nuesser et al. |
| 2005/0220636 A1 | 10/2005 | Henein et al. |
| 2007/0132587 A1 | 6/2007 | Smith et al. |
| 2007/0182578 A1 | 8/2007 | Smith |
| 2008/0041930 A1 | 2/2008 | Smith et al. |
| 2008/0238680 A1 | 10/2008 | Posamentier et al. |
| 2009/0243813 A1 | 10/2009 | Smith et al. |
| 2010/0045114 A1 | 2/2010 | Sample et al. |
| 2010/0052811 A1 | 3/2010 | Smith et al. |
| 2010/0076247 A1 | 3/2010 | Zilbershlag et al. |
| 2010/0081379 A1 | 4/2010 | Cooper et al. |
| 2010/0187913 A1 | 7/2010 | Smith et al. |
| 2012/0239118 A1 * | 9/2012 | Ozawa et al. .................. 607/61 |

* cited by examiner

FLEXIBLE GALVANIC PRIMARY AND NON GALVANIC SECONDARY COILS FOR WIRELESS COPLANAR ENERGY TRANSFER (CET)

RELATED APPLICATION

This application claims the benefit of and priority to U.S. Provisional Application No. 61/735,790, filed Dec. 11, 2012.

TECHNICAL FIELD

The invention generally relates to wireless energy transfer into the body of a patient to power wirelessly a device implanted within the body.

BACKGROUND

Congestive heart failure results from the inability of the heart to pump blood throughout the body at its normal pace, causing blood to flow a slower rate with increased pressure. As a result, the heart is unable to meet the oxygen and nutrient demands of an individual's vital organs. Heart failure may be caused by cardiomyopathy, heart valves damage, coronary heart disease, hypertension, and, in some cases, diabetes. Worldwide, more than a million patients currently suffer from congestive heart failure. In the United States alone, thousands of patients with congestive heart failure are candidates for heart transplantation or an electro-mechanical heart implant, such as a ventricular assist device.

Ventricular assist devices (VAD) are implantable electro-mechanical pumps that are used to partially or completely replace the function of a failing heart. Ventricular assist devices do not replace the heart entirely, but rather assist the right (RVAD) or left (LVAD) ventricle in their ability to pump blood. The choice of the device depends on the underlying heart disease and the pulmonary arterial resistances, which determines the load on the right ventricle. LVADs are more common, as RVADS are typically only necessary when pulmonary arterial resistance is very high.

VADs require a power source to operate the pump, and thus require connecting the VAD to an external power source. Traditionally, the VAD is directly connected to an external power source by a transcutaneous power line. The transcutaneous power line requires an exit site in the abdomen that provides a portal of entry for pathogens, and thus often results in device related infections.

As an alternative to transcutaneous power lines, wireless energy transfer systems were developed to deliver power to a VAD across an unbroken skin layer, thereby eliminating the possibility of infection associated with power lines. Wireless energy transfer systems include transcutaneous energy transfer systems (TET) and coplanar energy transfer (CET) systems. Both TET and CET systems include an external transmitter coil coupled to a power source that wirelessly delivers energy to an implanted receiver coil. The implanted receiver coil is connected to the implant and relays the received energy to the implant. The systems differ, in part, by how the transmitter and receiver coils are arranged with respect to each other. In TET systems, the transmitter coil located on the surface of the skin and is parallel to (separated by a distance z) and coaxial with the implanted receiver coil. In CET systems, the transmitter coil surrounds a part of a body (e.g. placed within a belt around the chest) and is coaxial with a receiver coil positioned within that part of the body. In this manner, coils of CET systems are not separated by a distance z (z=0) but are positioned within the same plane (i.e. coplanar).

The configurations of both TET and CET systems are essential to the efficiency of the power transfer from the transmitter coil to the receiver coil. For example, when the ratio of the distance z to the diameter D1 of the transmitter coil is greater than 0.1, the efficiency of the power transfer decreases. As such, wireless transfer systems are very sensitive to any misalignment and movement of the coils (which increases distance z). In addition, the efficiency of the power transfer decreases when the ratio of the diameter D2 of the receiver coil to the diameter D1 of the transmitter coil is greater than 1. Accordingly, the transmitter coil of current TET and CET systems must be in close proximity with and have a diameter similar to the receiver coil in order to provide efficient and safe energy transfer. This requires that a patient wear the transmitter coil coupled to the power source on his/her person at all times. Unfortunately, the power source can be bulky and uncomfortable, and wearing the transmitter coil reduces but does not always prevent axial and radial misalignment problems. Since misalignment may ultimately result in loss of power to the VAD, there is a need for improved wireless energy transfer systems.

SUMMARY

The invention provides a convertible wireless energy transfer system for supplying power to an implanted device that converts from a near power transfer configuration and a distant power transfer configuration. With both near and distant power configurations, convertible wireless energy transfer systems of the invention provide greater flexibility to individuals requiring wireless energy to power an implanted device. During near power transfer, a convertible inductive coil, worn by an individual, generates and inductively transmits electromagnetic power to an implanted receiver inductive coil. Near power transfer is ideal for when an individual desires mobility and thus requires wireless energy wherever the individual travels. The convertible inductive coil is typically coupled to a direct power source in order to generate and directly transmit electromagnetic power to the receiver coil. During distant power transfer, the convertible inductive coil transitions from direct power transfer to passive power transfer. For passive power transfer, the convertible inductive coil non-galvanically couples to the receiver inductive coil such that the convertible inductive coil and receiver inductive coil together form a single coupled receiver coil. The single coupled receiver coil is able to receive electromagnetic power generated and transmitted by a distant transmitter coil, which is located a distance from and not worn by the individual. Distant power transfer is ideal for when an individual is indoors, such as in a hospital, home, or office. In the distant power configuration, the convertible inductive coil may be decoupled from the direct power source, thereby providing greater comfort and ease of movement. In addition, the combined convertible inductive coil and receiver inductive coil (i.e. single coupled inductive coil) has a greater diameter than the receiver inductive coil alone, which increases the efficiency of the electromagnetic power transfer from the distant transmitter coil. The increased efficiency reduces power transfer issues associated with axial and radial misalignment.

According to certain aspects, a system of the invention for wirelessly powering an implant includes a convertible inductive coil and a receiver inductive coil. The convertible inductive coil is disposed externally on a body of a patient is configured to inductively transmit electromagnetic power.

The receiver inductive coil may be implanted within the body and associated with the implant to wirelessly receive electromagnetic power and provide that received power to the implant. The convertible inductive coil and the receiver inductive coil can be positioned for coplanar energy transfer or positioned for transcutaneous energy transfer. For electromagnetic power transmission, the convertible inductive coil is able to transition between direct electromagnetic power transfer and passive electromagnetic power transfer.

Direct electromagnetic power transfer is ideal for near power transfer, and passive electromagnetic power transfer is ideal for distant power transfer. During direct electromagnetic power transfer, the convertible inductive coil is coupled to a direct power source and generates and directly transfers electromagnetic power to the implanted receiver inductive coil. During passive electromagnetic power transfer, the convertible inductive coil non-galvanically couples to the receiver inductive coil such that the convertible inductive coil and receiver inductive coil operate together as a single inductive coil that receives inductively transmitted power from a distant transmitter inductive coil. Because the convertible inductive coil is non-galvanically coupled to the receiver inductive coil, the direct power source (such as a battery) can be removed from the convertible inductive coil.

The distant transmitter inductive coil generates and provides electromagnetic power to the non-galvanically coupled convertible inductive coil and receiver inductive coil, and can be positioned a distance from the convertible inductive coil and receiver inductive coil. In certain embodiments, the distant transmitter inductive coil is separated by a distance of at least 0.5 ft from the convertible inductive coil and the receiver inductive coil. The distant transmitter inductive coil does not have to be worn by the individual in order to effectuate electromagnetic power transfer. The distant transmitter inductive coil may be incorporated into an individual's surrounding. In some instances, the distant transmitter inductive coil is incorporated into one or more pieces of furniture, one or more portable cushions, one or more walls of a room, one or more walls of a shower, and/or within a vehicle.

Systems for wireless energy transfer of the invention can be used to power one or more implanted devices. The implanted device may be, for example, a ventricular assist device (VAD) or other medical device. If the device is a VAD, then the wirelessly-transferred power can be used to operate the pumping action of the VAD. The patient using a wireless energy transfer system can be a human or an animal, and the system can be used to power an implanted device located in any body part (such as arm, leg, head, or torso) of the patient. The convertible inductive coil, receiver inductive coil, and distant transmitter inductive coil can be formed from one or more turns of an electrically-conductive material (e.g. metal wire).

DETAILED DESCRIPTION

Figure 1:
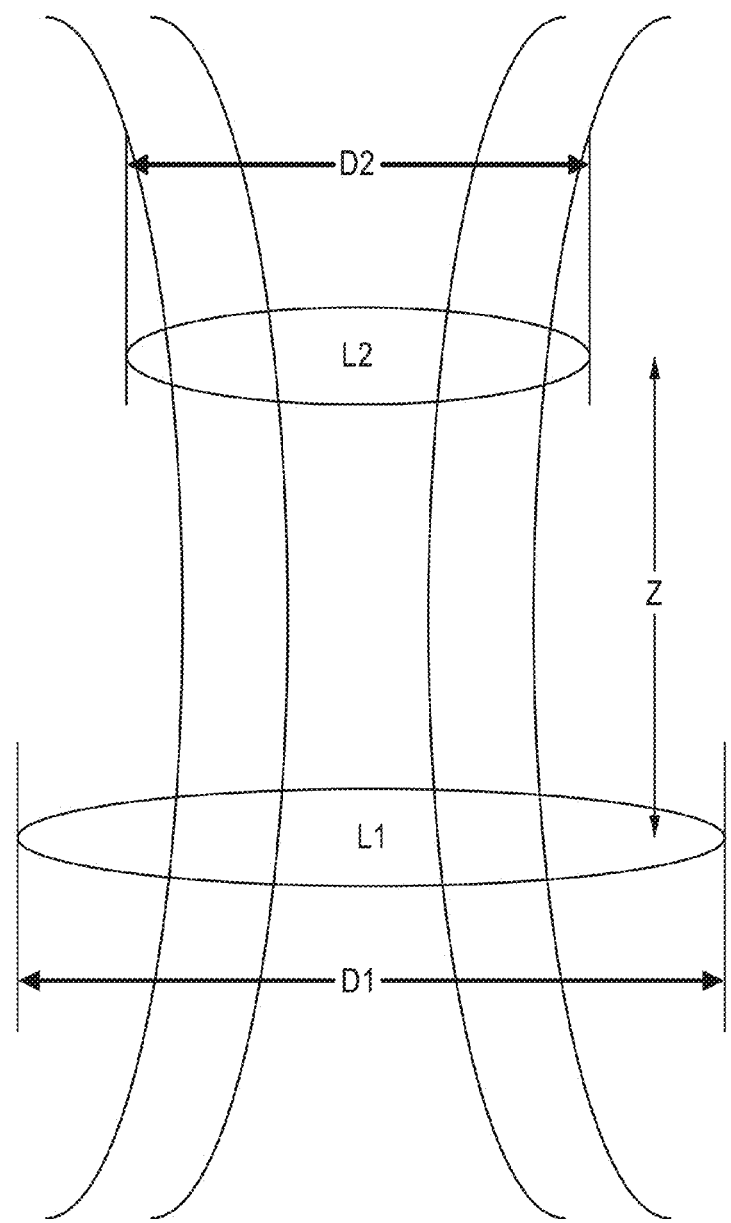
FIG. 1 schematically depicts a basic wireless energy transfer system.

The invention relates to a wireless energy transfer system that wirelessly provides energy to an internal implant using one or more transmitter inductive coils and one or more receiver inductive coil. According to certain aspects, a system of the invention for wirelessly powering an implant includes a convertible inductive coil and a receiver inductive coil. The convertible inductive coil is disposed externally on a body of a patient is configured to inductively transmit electromagnetic power. The receiver inductive coil may be implanted within the body and associated with the implant to wirelessly receive electromagnetic power and provide that received power to the implant. The convertible inductive coil and the receiver inductive coil can be positioned for coplanar energy transfer or positioned for transcutaneous energy transfer. For electromagnetic power transmission, the convertible inductive coil is able to transition between direct electromagnetic power transfer and passive electromagnetic power transfer. For direct electromagnetic power transmission, the convertible coil acts as a transmitter inductive coil that directly transmits electromagnetic power to an implanted receiver coil. For passive electromagnetic power transmission, the convertible coil non-galvanically couples to the implanted receiver coil to act as a single coupled receiver coil that receives electromagnetic power transmitter from a separate, distant transmitter coil.

Direct electromagnetic power transfer is ideal for near power transfer, and passive electromagnetic power transfer is ideal for distant power transfer. During direct electromagnetic power transfer, the convertible inductive coil is coupled to a direct power source and generates and directly transfers electromagnetic power to the implanted receiver inductive coil. During passive electromagnetic power transfer, the convertible inductive coil non-galvanically couples to the receiver inductive coil such that the convertible inductive coil and receiver inductive coil operate together as a single inductive coil that receives inductively transmitted power from a distant transmitter inductive coil. Because the convertible inductive coil is non-galvanically coupled to the receiver inductive coil, the direct power source (such as a battery) can be removed from the convertible inductive coil. The patient can be a human or an animal, and the part of the body can be the arm, leg, head, or torso of the patient. The device can be an implantable medical device such as a ventricular assist device (VAD), and the received power can be used to operate the pumping action of the VAD. The device can be another type of implantable medical device including, for example, a stent, a constant glucose meter (CGM), a blood-pressure sensing device, a pulse sensing device, a pacemaker, a digital camera, a nerve stimulator, or an ultrasound device.

According to certain aspects, a convertible inductive coil is external to and near the body, and can be provided in, on, or with a belt designed to be placed externally around a part of the body of a patient. The convertible inductive coil, when coupled to a direct power source, acts a transmitter inductive coil that inductively transfers wireless energy to the receiver inductive coil, which supplies power to the implanted device. When it is desirable to power the implant from a transmitter inductive coil that is a distance away from the body, the convertible inductive coil can be non-galvanically couple to the receiver inductive coil. For the non-galvanic coupling, the convertible inductive coil may be disconnected from the direct power source. The non-galvanic connection allows the receiver inductive coil and the convertible inductive coil to effectively operate a coupled receiving coil (e.g. the convertible inductive coil effectively operates as a resonance structure coupled to the receiver inductive coil). The coupled receiving coil effectively operates as a single unit to receive inductively transferred energy from a distant transmitter coil located a distance from the body. The distant transmitter coil can be used to push power to the coupled receiving coil. The distant transmitter inductive coil may be embedded or integrated into one's surroundings. For example, the distant transmitter inductive coil may be integrated into a pillow, a transportable cushion or padding, furniture (such as bedding, chairs, couches, etc.), one or more walls of a room, one or more walls of a shower, etc.

The described applications of the invention are for powering an implanted device. However, use of a convertible inductive coil that allows one to interchange between a convertible inductive coil and a distant transmitter coil for wireless power transfer can have other applications. For example, any application where it is desirable to provide power from a transmitter at both near and far distances, such as in wireless mobile and computing systems.

Wireless energy transfer systems of the invention rely on inductively coupled power transfer. The basic concept of an inductively coupled power transfer system involves inducing electric current through a wire to generate a magnetic field, and transferring that magnetic energy to a second wire. Typically, the wires are coiled in order to amplify the magnetic field. FIG. 1 schematically depicts a basic wireless energy transfer system. As shown in FIG. 1, the system includes a transmitter coil L1 and a receiver coil L2. Applying an alternating current in the transmitter coil L1 generates a magnetic field. When the receiver coil L2 is within the generated magnetic field of the transmitter coil L1, the generated magnetic field induces a current/voltage in the receiver coil L2, thereby allowing transfer of power. The receiver coil L2 may then be used to power a device or charge another battery.

Figure 2:
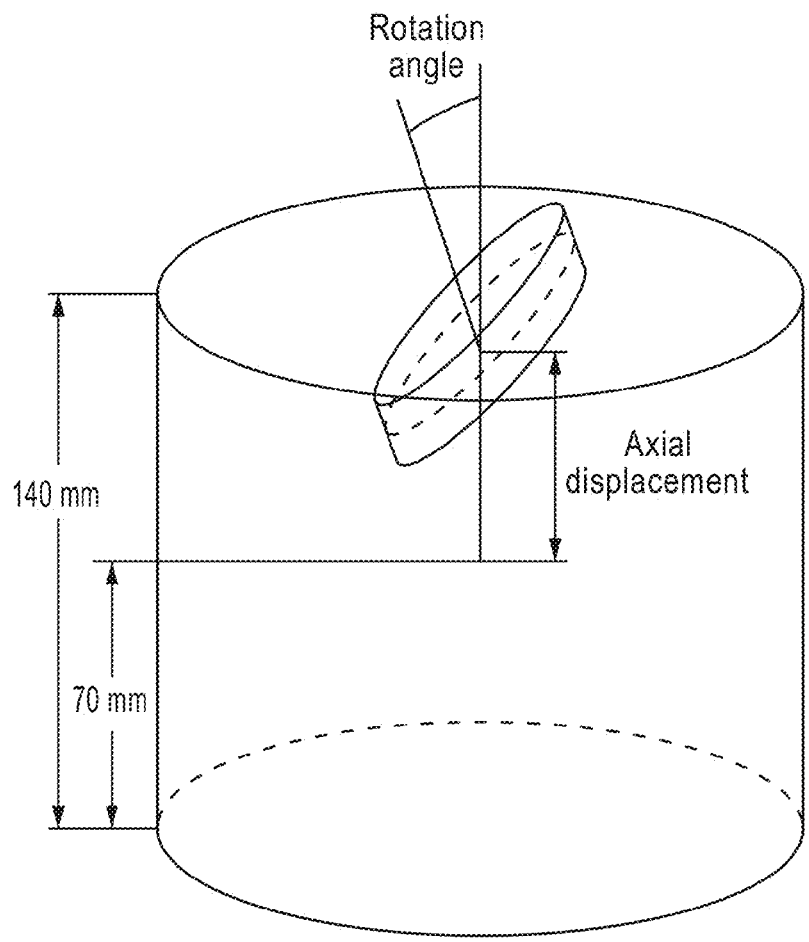
FIG. 2 further illustrates a basic wireless transfer system.

The efficiency of power transfer in the system outlined in FIG. 1 depends on the coupling (k) between the inductors and their quality (Q). The coupling (K) is determined by the distance (z) between coils (L1 and L2) and the relative size of their diameters (D2/D1). In addition, the relationship between the size of the coils (D1 and D2) relative to the distance (z) also factors into the efficiency of the coupling (K). The power transfer coupling is further determined by the shape of the coils (L1, L2) and the angle between them (as shown in FIG. 2).

When discussing receiver coils and transmitter coils, often the coil transmitting power is called the primary coil and the coil receiving power is called the secondary coil. As described herein, the terms transmitter coil, primary coil, transmitter inductive coil, etc. may be referred to describe the coil transmitting the electromagnetic power. Likewise, the coil receiving the electromagnetic power may be referred to as the secondary coil, receiver coil, receiver inductive coil, etc. Receiver and transmitter coils are typically one or more turns of an electrically conductive such as wire.

There are three basic systems that transfer energy inductively: a non-resonance system, a galvanically coupled resonance system, and a non-galvanically coupled resonance system. These systems may be utilized in aspects of the present invention, and are described hereinafter.

Figure 3:
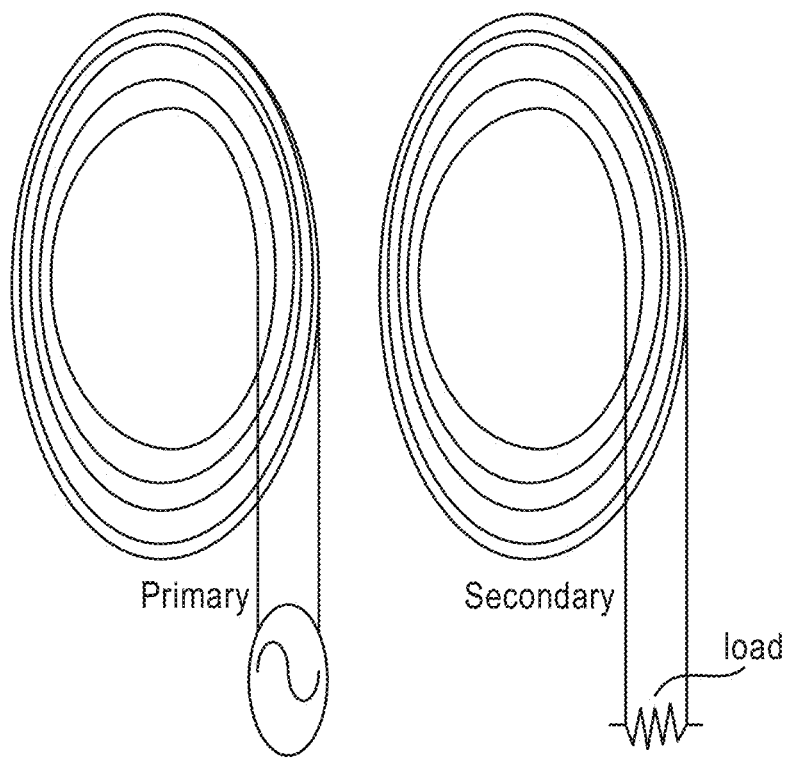
FIG. 3 illustrates a non-resonance system for electromagnetic power transfer.

FIG. 3 illustrates a non-resonance system for electromagnetic power transfer, known as a transformer. Transformers are one of the most basic wireless energy transfer systems that utilize primary and secondary coils. As shown, the primary coil is coupled to a power source (such sa a battery) that induces a current in the primary coil, and the secondary coil is coupled to a load, which may be a battery or a device. In a transformer, the primary and the second coils are close in distance (e.g. distance z is approximately 0) and similar in diameter (e.g. D2/D1 is approximately 1). Due to the small z and similar size, the transformer typically has good coupling (K).

When the distance between the primary and the second coil is greater than zero (i.e. z>0), or when the size of the primary or secondary coils are not the same (i.e. D2/D1 is greater than 1), the coupling of the coils diminishes, thereby reducing the efficiency of the power transfer. In order to improve efficiency, a resonance structure may be incorporated in the transmitter and/or receiver coils in order to avoid a significant drop in efficient and allow coupling despite the difference in size and distance between coils. From the beginning of wireless power transmission, resonance circuits/structures have been used to enhance the inductive power transmission. Even Nicola Tesla used resonances in his first experiments about inductive power transmission more than hundred years ago. Especially for systems with a low coupling factor, a resonant receiver can improve the power transfer. Resonant power transmission is a special, but widely used method of inductive power transmission and is limited by the same constraints of magnetic fields emissions and efficiency.

Figure 6:
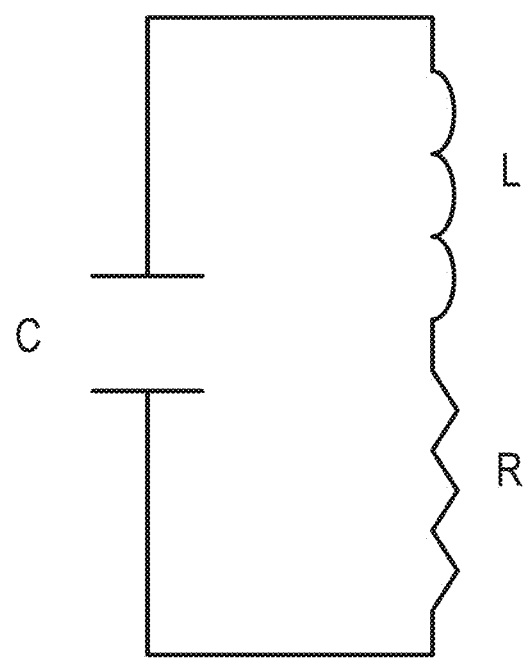
FIG. 6 illustrates circuitry of a resonance structure.

Resonance structures are also called electromagnetic resonators. Typical resonance structures include an inductor, a capacitor, and a resistor. FIG. 6 depicts an example of a resonance structure. In the circuit of the resonance structure, energy oscillates at the resonance frequency between the inductor and the capacitor and is dissipated in the resistor. The inductor involves the energy stored in the magnetic field and the capacitor involves energy stored in the electric field. The resonant frequency ($\omega_O$) and the quality factor (Q) for the resonance structure in FIG. 6 are:

$$\omega_0 = \frac{1}{\sqrt{LC}}$$

and $$Q = \frac{\omega_0}{|2\Gamma|} = \sqrt{\frac{L}{C}} \frac{1}{R} = \frac{\omega_0 L}{R}$$

The expression for the quality factor Q shows that decreasing the loss in the circuit, (reducing resistance R) increases the quality factor Q of the system.

Figure 4:
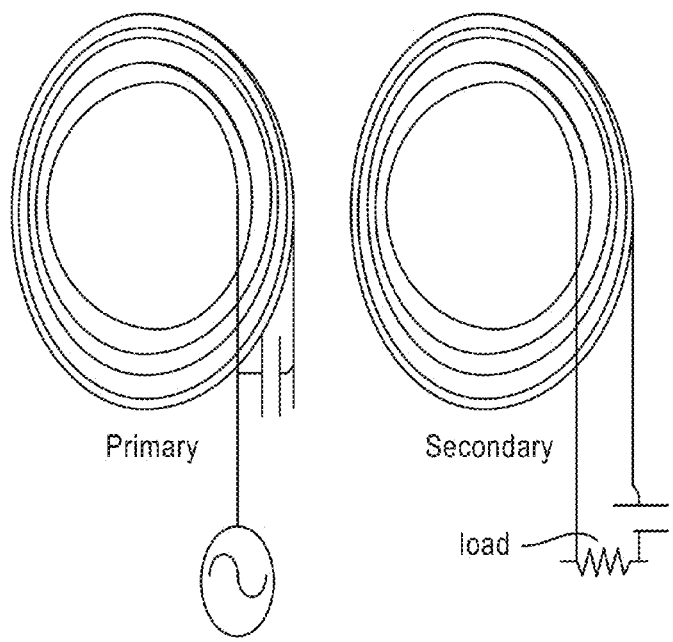
FIG. 4 depicts a wireless energy transfer system with directly coupled resonance structures.
Figure 5:
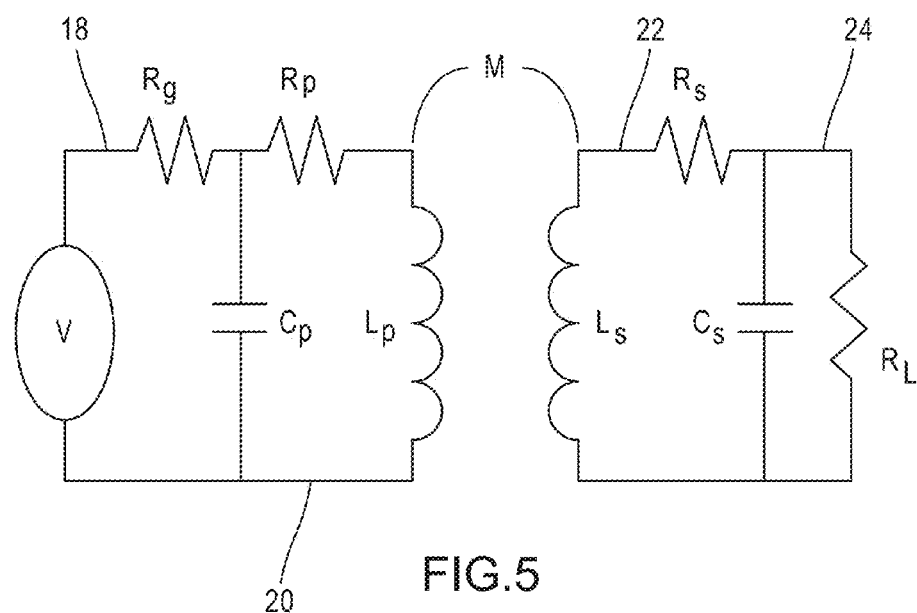
FIG. 5 depicts an exemplary circuit of the wireless energy transfer system of FIG. 4.

FIG. 4 illustrates a wireless energy transfer system in which the resonance structures are galvanically coupled to the transmitter coil and receiver coil. Although both the transmitter and receiver inductive coils are shown with resonance structures, the system can be altered such that only the primary transmitter coil or the second receiver coil include a resonance structure. FIG. 5 exemplifies a circuit for the resonant coupling depicted in FIG. 4. As shown in FIG. 5, the circuit includes primary coil 18 and a secondary coil 24. The primary coil 18 includes a voltage source (such as a battery), a voltage resistance $V_G$, and a resonant structure 20. The resonant structure 20 is galvanically coupled to the voltage source. The resonant structure 20 of the primary coil 18 includes a resistance $R_P$, a capacitor $C_P$, and an inductor L. The secondary coil includes a load $R_L$ (such as an implant or battery) and a resonant structure 22. The resonant structure 22 of the secondary coil includes a resistance $R_S$, a capacitor $C_S$, and an inductor $L_S$. The primary coil 18 is inductively coupled (shown by M) to the secondary coil 24. The resonance coupling of the circuit shown in FIG. 5 has significant loading by the source and load resistance, which results in low Q. As such, the receiver and transmitter inductive coils are substantially coplanar and similar in size.

Figure 9A:
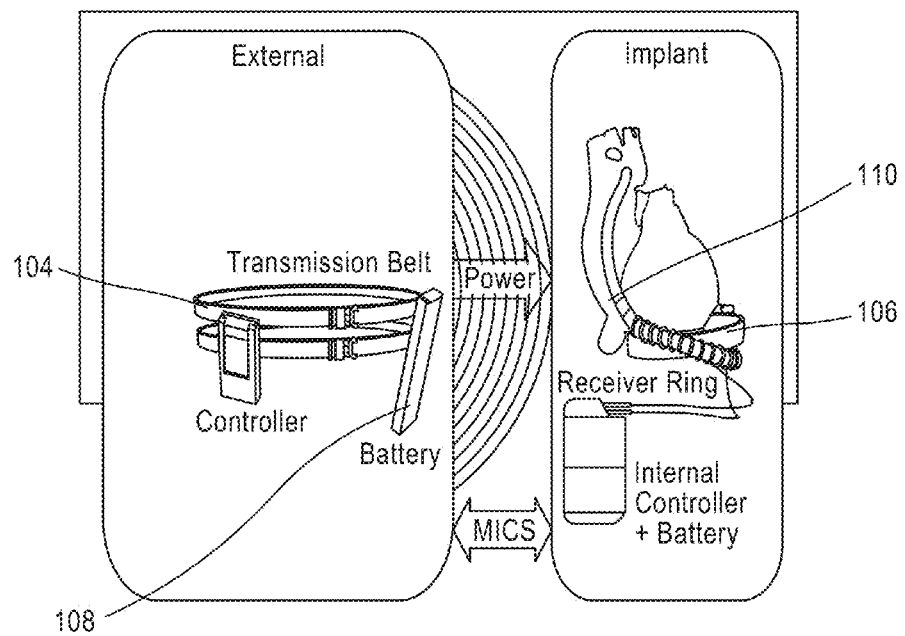
FIGS. 9A-9C illustrate configurations for near wireless energy transfer, according to certain embodiments.
Figure 9B:
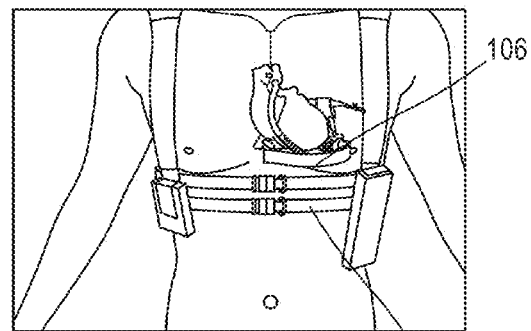
Figure 9C:
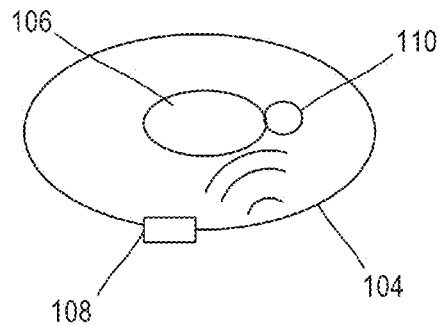
Figure 12:
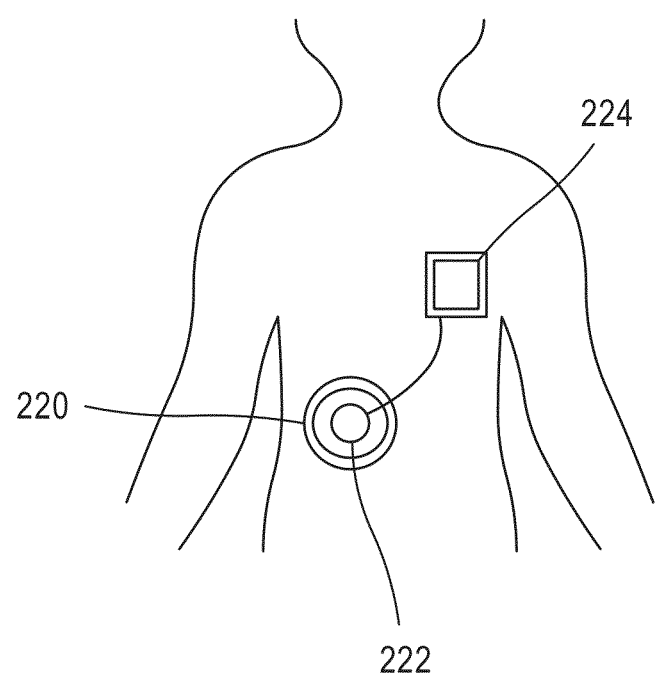
FIG. 12 illustrates a transcutaneous electromagnetic power transfer system.

The wireless transfer system depicted in FIG. 4 can be used for both Transcutaneous Energy Transfer (TET) and Coplanar Energy Transfer (CET) transfer systems. For TET transfer systems that use this configuration, the primary transmitter coil and the secondary receiver coil are similar in size and diameter D1, D2, but have a distance z>0 due to the need to pass through skin. FIG. 12 illustrates a TET transfer system, in which the transmitter coil 220 is placed externally on the skin such that the transmitter coil 220 is placed over and parallel to an implanted receiver coil 222. A distance z separates the external transmitter coil 220 and internal receiver coil 222. The implanted receiver coil 222 is connected to an implanted device 224. For CET transfer systems, the transmitter coil has a larger diameter D1 than the diameter D2 of the receiver coil, but the distance z is approximately 0 because the transmitter coil is coplanar with the receiver coil. FIGS. 9A-9C illustrate a CET transfer system.

Figure 7:
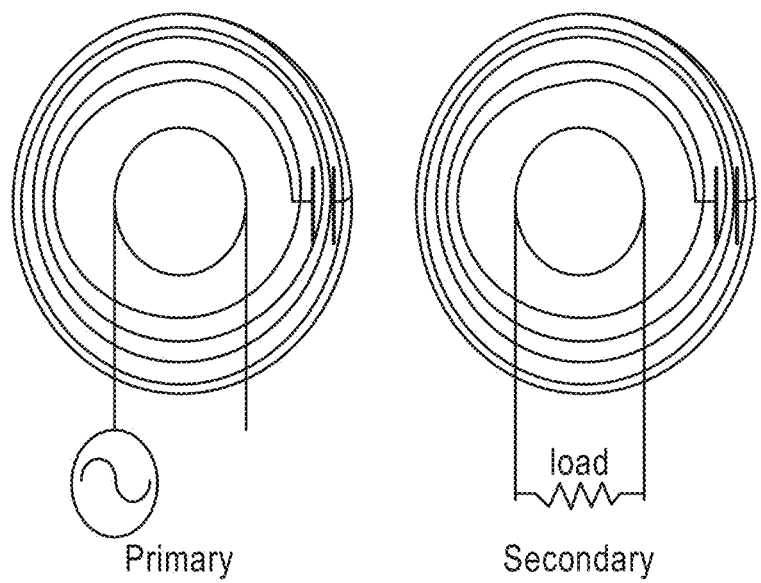
FIG. 7 depicts a wireless energy transfer system with inductively coupled resonance structures.

As an alternative to the direct coupling provided in the wireless power transfer system of FIG. 4, a primary and receiver coil can be inductively coupled (non-galvanically) to the resonance structures. FIG. 7 exemplifies such a configuration. As shown in FIG. 7, the power source is not galvanically connected to the primary resonance structure, and the power load is not galvanically connected to the secondary resonance structure. This architecture provides for non-radiative energy transfer by coupling of a resonance field evanescent tail of the primary resonance structure and a resonance field evanescent tail of the second resonance structure. The non-galvanic and inductive coupling of the transmitter and receiver with the resonance structures provides for parallel impendence. This results in high Q, despite a large distance z, because the resonance structures are not limited by the source resistance $R_S$ or the load resistance $R_L$. Non-galvanically coupled wireless transfer systems, such as that depicted in FIG. 7, are described in more detail in U.S. Pat. No. 8,097,983 as well as in publications: Cannon et al. Magnetic resonant coupling as a potential means for wireless power transfer to multiple small receivers. IEEE Transactions on Power Electronics 2009; 24; 1819-1825 and Kurs A., Moffatt R., Soljačić M. Simultaneous mid-range power transfer to multiple devices. Applied Physics Letters 2010; 96; 044102. Like the wireless transfer system depicted in FIG. 4, the wireless transfer configuration depicted in FIG. 7 may also be utilized in TET and CET systems.

Figure 8:
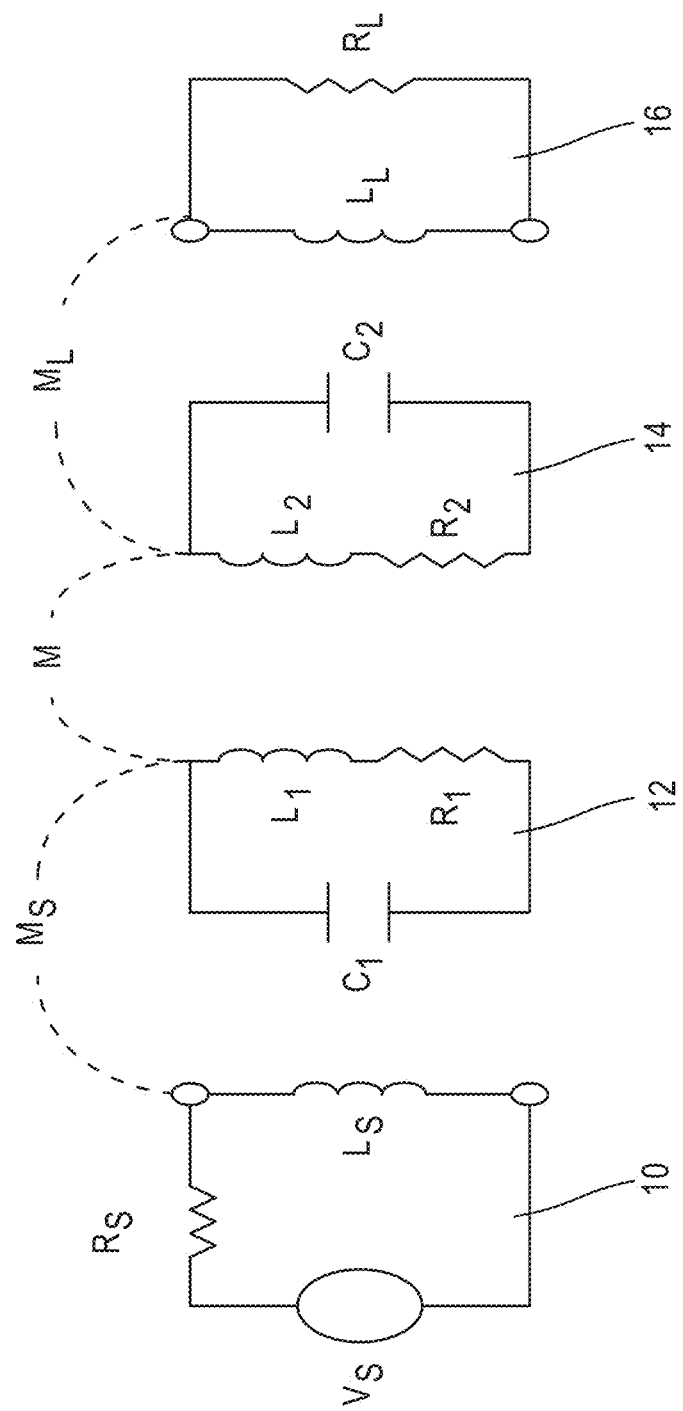
FIG. 8 depicts an exemplary circuit of the wireless transfer system of FIG. 7.

FIG. 8 exemplifies a circuit illustrating the inductive and non-galvanic coupling of the wireless energy transfer system shown in FIG. 7. A shown in FIG. 8, the transmitter 10 is coupled to a voltage source Vs, and includes inductive coil $L_S$. Inductive coil $L_S$ allows the transmitter 10 to inductively couple to the first resonant structure 12, as shown by $M_S$. The second resonant structure and is inductively coupled to the first resonant structure 12, as shown by M. The first resonant structure 12 is then inductively coupled to the second resonant structure 14, as shown by $M_L$. The second resonance structure 14 is inductively coupled to the receiver 16, which includes an inductive coil $L_L$. The primary receiver coil supplies the power transmitted from the transmitter, first resonant structure, and the second resonant structure to a load (as indicated by $R_L$). The load may be a device or a battery. A benefit of the system and circuits shown in FIGS. 7 and 8 is that the resonant structures 12 and 14 may be positioned a distance from the transmitter 10 and receiver 16, respectively. This effectively extends the wireless range of the primary transmitter coil and the secondary receiver coil (increases the distance Z).

As discussed in the Background, current wireless transfer systems used to power ventricular assist devices suffer from a couple of drawbacks. First, the external transmitter inductive coil must be in close proximity to the implanted receiver inductive coil in order to provide enough energy to consistently and efficiently power the implanted internal receiver. This is due to the inherent size limitations of the receiver inductive coil because it is implanted in the body and coupled to an implant (e.g., VAD). The need for close proximity requires a patient to wear the external transmitter inductive coil as well as the power source coupled to the external transmitter inductive coil. The power source is typically bulky and prone to heating, both of which can be uncomfortable to the wearer. Second, current wireless transfer systems may suffer from power loss due to translation of the external transmitter inductive coil with respect to the internal receiver inductive coil, which causes radial and/or axial misalignment.

Systems and methods of the invention overcome the problems associated with the prior wireless transfer systems by providing a convertible wireless power transfer system that utilizes the principles of one or more of the wireless transfer systems described above and outlined in FIGS. 3-8. Wireless transfer systems of the invention convert from a near power transfer configuration to a distant power transfer configuration. According to certain aspects, systems of the invention include a receiver inductive coil, a convertible inductive coil in close proximity with the receiver inductive coil, and a distant inductive coil. Preferably, the receiver inductive coil is implanted in an individual and coupled to an implanted device, the convertible inductive coil is worn by the individual, and the distant transmitter coil is a distance away from the individual. In certain instances, the distance between the distant transmitter coil and the individual is at least 0.5 ft, 1 ft, 1.5 ft, 2.0 ft, 2.5 ft, 3 ft, 3.5 ft, 4 ft, 4.5 ft, 5 ft, 10 ft, 15 ft, etc. During near power transfer, the convertible coil is coupled to a direct power source and acts as a transmitter coil that directly pushes wireless energy to the receiver coil. During distant power transfer, the convertible coil is decoupled from the direct power source and transitions into a non-galvanic connection with the receiver coil such that the convertible coil and receiver coil together act as a single coupled receiver coil. The distant transmitter coil is then used to generate and transmit the electromagnetic energy to the single coupled receiver coil (i.e. convertible coil and receiver coil). The single coupled receiver coil then transmits the received-inductively transferred electromagnetic energy to an implanted device coupled to the receiver coil.

The single coupled receiver coil effectively has a larger diameter than the receiver inductive coil by itself. As a result, the coupled receiver coil can then receive power from the distant transmitter coil with greater efficiency than the receiver coil by itself. This is because the convertible coil acts a relay coil between the distant transmitter coil and the receiver coil, and thus reduces loss of resonance energy that would occur between the distant transmitter coil and receiver coil but for the convertible coil. These aspects are described hereinafter in reference to the following FIGS. 9A-11D.

FIGS. 9A-9C illustrates the convertible wireless transfer system of the invention during near power transfer, according to certain aspects. FIG. 9A shows the transmission of wireless energy directly from a convertible coil 104 to an implanted receiver coil 106. FIG. 9C illustrates a schematic of FIG. 9A. During near power transfer, the convertible coil 104 is directly coupled to a power source 108, which allows the convertible coil 104 to generate electromagnetic power for direct power transfer. The generated electromagnetic energy of the convertible coil 104 is inductively transmitted directly to the receiver coil 106. The receiver coil 106 is coupled to the implant 110, and transmits the received wireless energy to the implant 110. Thus, the convertible coil 104 and the receiver coil 106 effectively act like an independent wireless transfer system with the convertible coil as the transmitter coil that inductively transfers power to the implanted receiver coil.

The convertible coil 104, as shown in FIGS. 9A-9C, is placed within a belt for CET energy transfer. FIG. 9B illustrates an individual wearing the belted convertible coil 104. However, the convertible coil 104 may be configured for TET energy transfer, such as in FIG. 12. The direct power source 108 of the convertible coil is typically a battery.

The convertible coil 104 and the receiver coil 106 of the near power transfer configuration can be designed to transmit wireless energy using any one or combination of wireless energy transfer configurations shown in FIGS. 3-5 and 7-8. In certain embodiments, the convertible coil 104 and/or receiver coil 106 do not include a resonance structure (see FIG. 3). In certain embodiments, the convertible coil 104 and/or receiver coil 106 include a resonance structure (see FIGS. 4-5 and 7-8). The resonance structure of the convertible coil 104 and/or the receiver coil 106 can be directly coupled (FIGS. 4-5) and/or inductively coupled (FIGS. 7-8) to the receiver coil 106 and convertible coil 104.

Figure 10A:
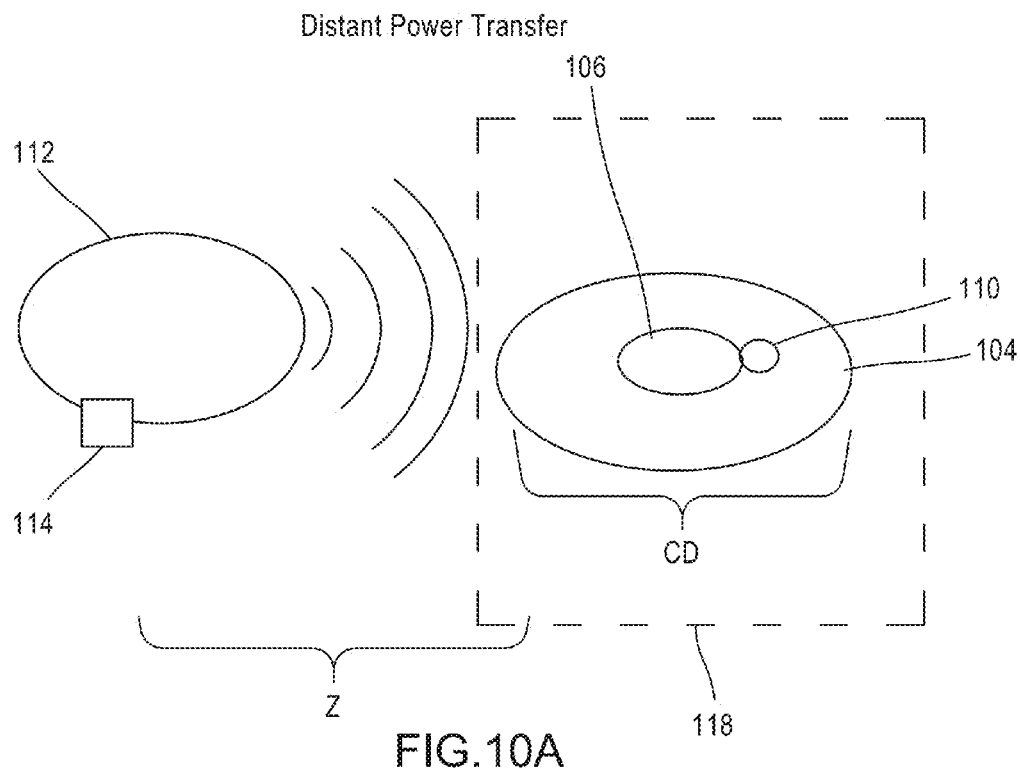
FIGS. 10A-10B illustrate configurations for distant wireless energy transfer, according to certain embodiments.
Figure 10B:
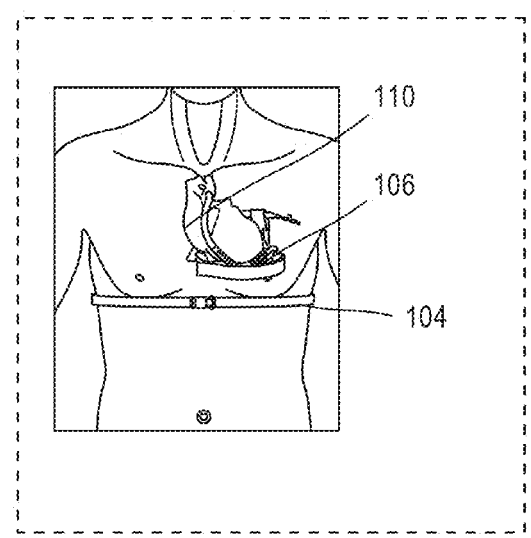

According to aspects of the invention, the convertible wireless power system can convert from a near power transfer configuration (shown in FIGS. 9A-9C) to a distant power transfer configuration (FIGS. 10A-10B). FIG. 10A illustrate the convertible wireless power system in the distant power transfer configuration. In this configuration, a distant transmitter coil 112 is used to generate and push wireless energy, and the convertible coil 104 converts into passive power transfer mode. During passive power transfer, the convertible coil 104 passively relays wireless energy received from the distant transmitter coil 112 to the receiver coil. The passive relay of wireless energy effectively converts the convertible coil 104 and the receiver coil 106 into a single coupled receiver coil (as indicated by box 118).

In order to convert the convertible coil 104 into the passive power transfer mode, the direct power source 108 is removed or disconnected from the convertible coil 104. The direct power source 108 can be disconnected from the convertible coil 104 by, for example, using a short. FIG. 10B depicts the convertible coil 104 in a belt worn by an individual with the battery removed. When decoupled from the direct power source 108, the convertible coil 104 inductively and non-galvanically couples to the implanted receiver coil 106 such that the convertible coil 104 and implanted receiver coil 106 effectively operate as a single combined receiver coil (as indicated by the box 118).

The single combined receiver coil 118 has a combined diameter CD that is larger than the diameter D1 of the receiver coil 106 alone, thereby increasing the efficiency of the wireless energy transfer. This allows the distance Z between the receiver coil 106 and a distant transmitter coil 112 to increase without losing efficiency in the power transfer, and reduces alignment issues. In certain instances, the distance between the distant transmitter coil and the single combined receiver coil is 0.5 ft, 1 ft, 1.5 ft, 2.0 ft, 2.5 ft, 3 ft, 3.5 ft, 4 ft, 4.5 ft, 5 ft, 10 ft, 15 ft, etc. The convertible coil 104, during passive power transfer, can be considered a relay resonance structure (similar to the resonance structures shown in FIG. 7).

For distant wireless energy transfer, the distant transmitter coil 112 is coupled to a power source 114. With the power source 114, the distant transmitter coil 112 generates and transmits wireless energy to the convertible coil 104 and receiver coil 106. In certain embodiments, the power source 114 is a battery. The convertible coil 104 receives wireless energy from the distant transmitter coil, and passively transmits the received wireless energy to the receiver coil 106 through induction. During passive transfer, the convertible coil 104 and receiver coil 104 effectively operates a single combined receiver coil. The receiver coil 106 transmits the received wireless energy to the implant 110. A benefit of distant wireless energy transfer is that an individual, who require wireless energy transfer for implanted devices, can remove a direct power source from the convertible coil when in the presence of the distant transmitter coil. This increases flexibility and comfort to the individual.

The distant transmitter coil 112, the convertible coil 104, and the receiver coil 106 of the distant power transfer configuration can be designed to transmit wireless energy using any one or combination of wireless energy transfer configurations shown in FIGS. 3-5 and 7-8. In certain embodiments, the distant transmitter coil 112, the convertible coil 104, and/or receiver coil 106 do not include a resonance structure (see FIG. 3). In certain embodiments, the distant transmitter coil 112, the convertible coil 104 and/or receiver coil 106 include a resonant structure (see FIGS. 4-5 and 7-8). The resonant structure of the convertible coil 104 and/or the receiver coil 106 can be directly coupled (FIGS. 4-5) or inductively coupled (FIGS. 7-8) to the receiver coil 106 and convertible coil 104.

Figure 11A:
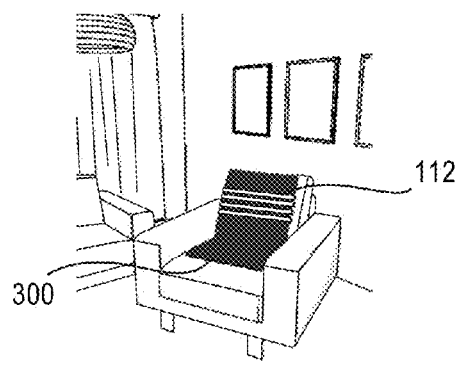
FIGS. 11A-11D illustrate various distant transmitter inductive coils, according to certain embodiments.
Figure 11B:
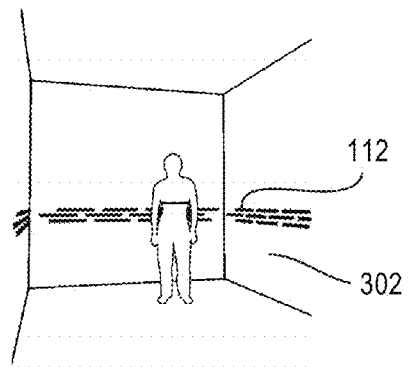
Figure 11C:
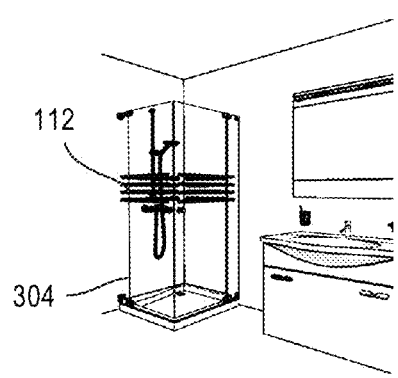
Figure 11D:
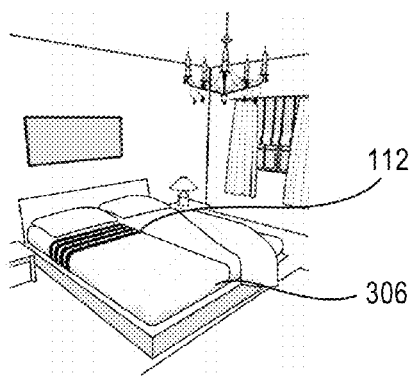

The distant transmitter coil 112 can have several different configurations. The distant transmitter coil 112 can be placed on or embedded in one or more objects (furniture, portable cushions, etc.), a vehicle, or one or more walls of room. Exemplary configurations for the distant transmitter coil 112 are shown in FIGS. 11A-11D. FIG. 11A illustrates a distant transmitter coil 112 placed in a portable cushion 300. Alternatively, the distant transmitter coil 112 can be embedded directly into the furniture. FIG. 11B depicts a distant transmitter coil 112 embedded in or placed on one or more walls 302 of a room. FIG. 11C illustrates a distant transmitter coil 112 embedded in or placed on one or more walls of a shower 304. FIG. 11D illustrates a distant transmitter coil 112 embedded in or placed on a bed 306. In addition, one or more distant transmitter coil 112 can be used to push power to the convertible coil 104 and receiver coil 106 for powering an implanted device. For example, an individual may use distant transmitter coils placed in both a portable cushion and in the walls of a room in order to electromagnetically power his/her implanted device. In addition, an individual may switch from one or more distant transmitter coils 112 depending on the individual's location (e.g., from room to room) and depending on the activity (showering, sleeping, watching TV). By using one or more distant transmitter coils 112, an individual is allowed to have freedom of movement and to transition between one or more electromagnetic power sources depending on the activity.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A system for wirelessly powering an implant, comprising:
   a convertible inductive coil configured to be disposed externally on a body of a patient, to inductively transmit electromagnetic power, and to transition between direct power transfer and passive power transfer; and
   a receiver inductive coil configured to be implanted within the body and associated with the implant to wirelessly receive the inductively transferred power and provide that received power to the implant;
   the convertible inductive coil configured to, during passive power transfer, couple to the receiver inductive coil such that the convertible inductive coil and receiver inductive coil operate together as single receiver inductive coil that receives inductively transferred power from a distant transmitter inductive coil;
   the convertible inductive coil configured to, during direct power transfer, generate electromagnetic power and inductively transmit the electromagnetic power to the receiver inductive coil.

2. The system of claim 1, wherein the convertible inductive coil, during passive power transfer, is non-galvanically connected to the receiver inductive coil.

3. The system of claim 2, wherein the convertible transmitter inductive coil, during passive power transfer, is disconnected from a direct power source.

4. The system of claim 3, wherein the direct power source is a battery.

5. The system of claim 1, wherein the convertible inductive coil, during direct power transfer, generates the inductively transferred power.

6. The system of claim 1, wherein the convertible inductive coil, during direct power transfer, is coupled to a direct power source.

7. The system of claim 6, wherein the direct power source is a battery.

8. The system of claim 1, wherein the convertible inductive coil is disposed partially around a part of the patient's body and the receiver inductive coil is implanted within that part of the patient's body.

9. The system of claim 1, wherein the convertible inductive coil is in a plane parallel to the receiver inductive coil.

10. The system of claim 1, wherein the distant transmitter inductive coil is a distance of at least 0.5 ft. or more from the convertible inductive coil and the receiver inductive coil.

11. The system of claim 1, wherein the distant transmitter inductive coil is embedded in a portable cushion.

12. The system of claim 1, wherein the distant transmitter inductive coil is embedded in a piece of furniture.

13. The system of claim 1, wherein the distant transmitter inductive coil is embedded in at least one wall of a room.

14. The system of claim 1, wherein the distant transmitter inductive coil is embedded in at least one wall of a shower.

15. The system of claim 1, wherein the implant is an implantable ventricular assist device (VAD).

16. A convertible inductive coil system associated with a wirelessly-powered implantable device, the system comprising a first inductive coil and a second inductive coil, the first inductive coil configured to be disposed externally on a body of a patient and releaseably coupled to a power source, the second inductive coil configured to be implanted within the body and associated with the implant, the first inductive coil, when coupled to and powered by the power source, is a transmitter inductive coil configured to inductively transmit power to the second inductive coil, the first inductive coil, when decoupled from the power source, couples to the second inductive coil via a non-galvanic connection such that the first inductive coil and second inductive coil operate as a single receiver inductive coil, the single receiver inductive coil configured to receive inductively-transferred power from a distant transmitter inductive coil.

17. The system of claim 16, wherein the first inductive coil is disposed partially around a part of the patient's body and the second inductive coil is implanted within that part of the patient's body.

18. The system of claim 16, wherein the first inductive coil is in a plane parallel to the second inductive coil.

19. The system of claim 16, wherein the distant transmitter inductive coil is embedded in a portable cushion.

20. The system of claim 16, wherein the distant transmitter inductive coil is embedded in a piece of furniture.

21. The system of claim 16, wherein the distant transmitter inductive coil is embedded in at least one wall of a room.

22. The system of claim 16, wherein the distant transmitter inductive coil is embedded in at least one wall of a shower.

23. The system of claim 16, wherein the implantable device is a ventricular assist device (VAD).

* * * * *